United States Patent

Kasat et al.

[11] Patent Number: 6,165,480
[45] Date of Patent: Dec. 26, 2000

[54] COSMETIC SOAP-GELLED STICK COMPOSITION HAVING STABILITY AT HIGHER TEMPERATURES

[75] Inventors: Radhakrishna B. Kasat, Bellemead; Bhalchandra D. Moghe, Edison, both of N.J.

[73] Assignee: Colgate Palmolive Company, New York, N.Y.

[21] Appl. No.: 08/264,073

[22] Filed: Jun. 22, 1994

[51] Int. Cl.⁷ .................. A61K 7/02; A61K 7/32; A61K 7/48
[52] U.S. Cl. ................ 424/401; 424/65; 514/944
[58] Field of Search .......... 424/401, 65, DIG. 5; 514/944; 252/367, 315.01, 315.4; 516/104, 109, 902

[56] References Cited

U.S. PATENT DOCUMENTS

| | | | |
|---|---|---|---|
| 4,107,289 | 8/1978 | Kaufman | 424/45 |
| 4,120,948 | 10/1978 | Shelton | 424/66 |
| 4,252,789 | 2/1981 | Broad | 424/65 |
| 4,322,400 | 3/1982 | Yuhas | 424/59 |
| 4,382,079 | 5/1983 | Marshener | 424/65 |
| 4,504,465 | 3/1985 | Sampson et al. | 424/65 |
| 4,617,185 | 10/1986 | DiPietro | 424/65 |
| 4,702,916 | 10/1987 | Geria | 424/400 |
| 4,759,924 | 7/1988 | Luebbe et al. | 424/65 |
| 4,944,937 | 7/1990 | McCall | 424/65 |
| 5,114,717 | 5/1992 | Kuznitz et al. | 424/401 |
| 5,128,123 | 7/1992 | Brewster et al. | 424/65 |
| 5,232,689 | 8/1993 | Katsoulsi et al. | 424/66 |
| 5,858,336 | 1/1999 | Graf et al. | 424/65 |

*Primary Examiner*—Robert H. Harrison
*Attorney, Agent, or Firm*—William I. Soloman; Richard J. Ancel

[57] ABSTRACT

Disclosed is a cosmetic soap-gelled solid stick composition, which maintains its shape and aesthetic properties even when stored at high temperatures for long periods of time. The composition includes at least one alcohol (monohydric and/or polyhydric), water, and a soap gelling agent, the alcohol being a solvent for the soap gelling agent, the soap gelling agent being alkali metal (e.g., sodium) salts of fatty acids having $C_{12}$–$C_{22}$ carbon chain length. At least 65% by weight, of the total weight of the soap gelling agent, are alkali metal salts of fatty acids having $C_{20}$–$C_{22}$ carbon chain length.

26 Claims, No Drawings

COSMETIC SOAP-GELLED STICK COMPOSITION HAVING STABILITY AT HIGHER TEMPERATURES

BACKGROUND OF THE INVENTION

The present invention is directed to a soap-gelled stick composition, used as a base for incorporation of various active ingredients, including deodorant active ingredients, to form various stick products, including deodorant sticks. The active ingredient is incorporated in the base composition, and is applied, e.g., to the skin when the composition having the active ingredient incorporated therein is rubbed against the skin, as known with conventional sticks. Moreover, the present invention is directed to a deodorant soap-gelled solid stick, having a deodorant active material incorporated in the soap-based gel stick composition. In particular, the present invention relates to a soap-based gel stick composition which maintains its physical form and aesthetic qualities over extended periods of time, even under high-temperature climatic conditions (that is, a gel stick composition that is stable even under hot environmental (weather or storage) conditions).

Soap-gelled solid stick compositions, for applying active ingredient to, e.g., skin of a human, are known. Current deodorant sticks in the market place (both in the United States and outside the United States) are based on sodium stearate as the soap gelling agent, the deodorant sticks having a melting temperature not greater than 59° C. When exposed to hot climatic conditions, these stick products melt and/or deform, leading to aesthetically inferior products (that is, products having poor surface characteristics, exhibiting syneresis, etc.). Of course, the problem of an inferior product in hot climatic conditions is particularly acute in hot regions of the world, such as in the Far East and Latin America.

U.S. Pat. No. 4,252,789 to Broad discloses a soap-based stick composition for applying active ingredients to the skin, the composition being water-based and consisting essentially of from about 3% to about 10% by weight of a mixture of sodium stearate and sodium palmitate in a weight-ratio range from about 1:1 to about 9:1; from about 0.1% to about 3.0% by weight of a soap-compatible germicide; from about 0.1% to about 0.5% by weight of a compound selected from the class consisting of polyethylene imine and ethoxylated polyethylene imine, the compound having an average molecular weight from about 40,000 to about 100,000; and the balance being water. This patent discloses that adding polyethylene imine or ethoxylated polyethylene imine causes the resulting stick to shrink slightly on setting up, rather than expanding, so that such a stick is more readily extruded from the cylindrical case typically used for deodorant sticks. Furthermore, the temperature stability of the resulting stick is enhanced. This patent further discloses that small amounts of the salts of myristic and oleic acid are typically present in commercially available sodium stearate and sodium palmitate; and that while sodium myristate in concentrations below 5% by weight of the total soap concentration have little effect upon the stick, sodium oleate should be avoided as much as possible and should typically not be present in concentrations in excess of about 2% by weight of the total soap concentration.

Note that U.S. Pat. No. 4,252,789 requires additional materials, including an imine compound, in order to enhance temperature stability.

U.S. Pat. No. 4,504,465 to Sampson, et al discloses cosmetic compositions in the form of solid sticks, containing, as essential components, (1) a polyhydric aliphatic alcohol containing 2 or 3 carbon atoms and from 2 to 3 hydroxyl groups, suitable polyhydric alcohols including ethylene glycol, propylene glycol, trimethylene glycol and glycerine; (2) a gel-forming agent, which is a sodium or potassium salt (soap) of fatty acids containing from about 14 to 18 carbon atoms; and (3) an ethylene oxide and/or propylene oxide condensation product having the formula:

$$R(OC_3H_6)_a(OC_2H_4)_bOH,$$

wherein R is either hydrogen or a hydrocarbon chain having from about 2 to 20 carbon atoms, preferably from about 4 to 18, a and b are each from 0 to 35 and a+b is from 5 to 35. This patent discloses that the fatty acid portion of the soap gel-forming agents should be pure unsaturated or saturated higher fatty acids having a $C_{14}$ to $C_{18}$ backbone; and that suitable mixtures of such acids can be employed provided that such mixtures are free from significant proportions of other fatty acids of higher or lower chain length which substantially adversely affect or neutralize the desired gel-forming effects.

This patent discloses that examples of fatty acids useful in synthesizing the gel-forming agents include myristic, palmitic, stearic, oleic, linoleic, linolenic, margaric and mixtures of such acids; and that naturally occurring sources of such fatty acids include coconut oil, beef tallow, lanolin, fish oil, bees wax, palm oil, peanut oil, olive oil, cotton seed oil, soy bean oil, corn oil, rapeseed oil, rosin acids and greases.

Similarly, U.S. Pat. No. 4,759,924 to Luebbe, et al teaches a cosmetic composition in the form of solid sticks, having clarity and including from about 40% to about 70% of a polyhydric aliphatic alcohol, from about 3% to about 10% of a soap, from about 1% to about 20% of a hydro-alcoholic soluble emollient, and water. The hydro-alcoholic soluble emollient has the following formula:

$$R(OC_3H_6)_a(OC_2H_4)_bOH,$$

wherein R is either hydrogen or a hydrocarbon chain having from about 1 to 18 carbon atoms, and $a/(a+b) \leq 0.5$. This patent discloses that the soaps are preferably sodium, potassium and aluminum salts (i.e., soaps) of fatty acids containing from about 14 to 18 carbon atoms.

Each of the following U.S. patents also disclose soap-gelled cosmetic stick compositions:

(1) U.S. Pat. No. 4,944,937 to McCall;
(2) U.S. Pat. No. 4,617,185 to DiPietro;
(3) U.S. Pat. No. 4,702,916 to Geria;
(4) U.S. Pat. No. 5,114,717 to Kuznitz, et al; and
(5) U.S. Pat. No. 5,128,123 to Brewster, et al. The soap gelling agent in each of these patents is described as including, inter alia, sodium salts of higher fatty acids, that is, acids having from 12 to 22 carbon atoms. It is further disclosed in each of U.S. Pat. No. 4,617,185; U.S. Pat. No. 5,114,717; and U.S. Pat. No. 5,128,123 that preferably $C_{14}$–$C_{18}$, or $C_{16}$–$C_{18}$, fatty acids are utilized as the fatty acid component of the soap gelling agents. None of these five U.S. patents are concerned with providing a gel stick that is stable and maintains its form and aesthetic qualities under hot climatic conditions. Moreover, none of these five U.S. patents even discloses any problems arising in connection with cosmetic or deodorant soap-gelled solid stick compositions maintained under hot conditions.

SUMMARY OF THE INVENTION

It is an object of the present invention to provide a soap-gelled solid stick composition forming a base material for incorporating active ingredient therein, which maintains its physical form and aesthetic qualities under hot environmental conditions (for example, under hot storage conditions, hot climatic conditions, etc.), including when the active ingredient has been incorporated therein.

It is a further object of the present invention to provide a cosmetic, soap-gelled, solid stick composition, having active ingredient incorporated therein (depending on the active ingredient incorporated, a deodorant soap-gelled solid stick composition, a sunscreen soap-gelled solid stick composition, an insecticide soap-gelled solid stick composition, etc.), which maintains its physical form and aesthetic qualities under hot environmental conditions.

It is a further object of the present invention to provide deodorant solid stick composition, gelled using a soap gel-forming agent, which maintains its physical form and aesthetic qualities (that is, is stable) under hot environmental conditions.

It is a further object of the present invention to provide a cosmetic solid stick composition, gelled using a soap gel-forming agent, having a high melting point (for example, a melting point greater than 59° C.).

The foregoing objects are achieved by using, as the soap gel-forming agent, alkali metal salts of fatty acids wherein at least 65% by weight, of the total weight of the soap gel-forming agent in the composition, are alkali metal salts of fatty acids having $C_{20}$–$C_{22}$ (e.g., $C_{20}$ and/or $C_{22}$) carbon chain length. Desirably, the soap gel-forming agent is sodium salts of higher fatty acids wherein at least 65% by weight of the gel-forming agent are sodium salts of $C_{20}$ and/or $C_{22}$ fatty acids. These soap gel-forming agents are, preferably, sodium salts of saturated fatty acids, with at least 65% by weight of the soap gel-forming agent being the sodium salt of behenic acid and/or the sodium salt of arachidic acid.

Specifically, the compositions, in the form of solid sticks, according to the present invention, include monohydric and/or polyhydric alcohol, water, and also include alkali metal (e.g., sodium) salts of fatty acids as the soap gel-forming agent, the alkali metal salts of fatty acids including at least 65% by weight, of the total weight of the salts, of an alkali metal salt of arachidic acid ($C_{20}$ carbon chain length) and/or an alkali metal salt of behenic acid ($C_{22}$ carbon chain length). The remaining soap gel-forming agent can be alkali metal salts (e.g., sodium salts) of $C_{12}$–$C_{18}$ fatty acids. Cosmetic compositions according to the present invention incorporate an active ingredient in the previously disclosed composition containing monohydric and/or polyhydric alcohol, water and the soap gel-forming agent.

As indicated previously, at least 65% of the soap gel-forming agent is an alkali metal (e.g., sodium) salt of arachidic acid and/or of behenic acid. However, all of the soap gel-forming agent (i.e., 100% of the soap gel-forming agent) can be the alkali metal (e.g., sodium) salt of the $C_{20}$ fatty acid and/or of the $C_{22}$ fatty acid.

In forming a deodorant soap-gelled solid stick composition according to the present invention, the composition can include conventional fragrance and conventional active ingredients (such as Triclosan). Of course, compositions according to the present invention can include other active ingredients than deodorant active ingredients, such as sunscreens, insecticides, etc., whereby the solid sticks will be, respectively, sunscreen sticks, insecticide sticks, etc.

The compositions according to the present invention can include optional materials, such as polyols, fatty alcohols, alkanolamides, color, essential oils and fragrances, soluble inorganic salts of sodium or potassium, etc., and other conventional optional ingredients known in the art.

By the present invention a soap-gelled solid stick can be provided that can be stored at 120° F. while maintaining a satisfactory shape and size, and maintaining satisfactory aesthetic qualities (including avoiding syneresis), after three months of storage.

Thus, a cosmetic soap-gelled solid stick composition is achieved, having a melting point greater than 59° C., and which is stable (in physical form and in aesthetic qualities) under hot conditions, for extended periods of time.

DETAILED DESCRIPTION OF THE INVENTION

While the invention will be described in connection with specific and preferred embodiments, it will be understood that it is not intended to limit the invention to those embodiments. To the contrary, it is intended to cover all alterations, modifications and equivalents as may be included within the spirit and scope of the invention as defined by the appended claims.

Throughout the present specification, where compositions are described as including or comprising specific components, it is contemplated by the inventors that compositions of the present invention also consist essentially of, or consist of, the recited components. Accordingly, throughout the present disclosure any described composition can consist essentially of, or consist of, the recited components.

The present invention contemplates a soap-gelled solid stick composition, including cosmetic compositions such as a deodorant soap-gelled solid stick composition, including (1) at least one polyhydric and/or monohydric alcohol, as a solvent, (2) water, and (3) a soap gelling agent, the soap gelling agent including an alkali metal salt of fatty acids (e.g., saturated fatty acids), the fatty acid component of the alkali metal salt having a specific distribution. More particularly, the alkali metal salts of the fatty acids include at least 65% by weight, of the total weight of the soap, of alkali metal salt of $C_{20}$ and/or $C_{22}$ fatty acid (e.g., alkali metal salts of arachidic acid and/or of behenic acid). Up to and including 100% by weight, of the total weight of the soap, can be such alkali metal salts of $C_{20}$ and/or $C_{22}$ fatty acid. However, the remainder of the soap can be alkali metal salts of $C_{12}$–$C_{18}$ fatty acids.

Utilizing a stick gelled by a gel-forming agent which is at least 65% by weight of alkali metal salts of $C_{20}$ and/or $C_{22}$ fatty acid, a soap-gelled solid stick composition is achieved having a melting point greater than 59° C. Moreover, such stick maintains a stable physical form, and maintains its aesthetic properties, even under hot conditions (for example, the composition can be stored at 120° F. while maintaining a satisfactory shape and/or size even after three months).

The alcohol solvent utilized according to the present invention preferably is selected from those which are a solvent for the soap gelling agent and are substantially safe for application to human skin, and can be either a polyhydric alcohol or monohydric alcohol. Illustrative alcohols include monohydric alcohols such as ethyl alcohol, and polyhydric alcohols such as sorbitol, glycerine, propylene glycol, dipropylene glycol, etc. These are illustrative alcohols, and are not limiting. A preferred polyhydric alcohol is propylene glycol. Mixtures of these alcohols can also be utilized. For example, a mixture of propylene glycol and dipropylene glycol can be utilized as the solvent system for the soap gel-forming agent.

Various monohydric and polyhydric alcohols used in cosmetic soap-gelled solid stick compositions (including deodorant soap-gelled solid stick compositions) are disclosed in U.S. Pat. No. 4,382,079 and U.S. Pat. No. 4,322,400 (note that the polyhydric alcohols are designated as "polyhydroxyl compounds" in U.S. Pat. No. 4,322,400), and can be utilized herein. The contents of each of U.S. Pat. No. 4,382,079 and No. 4,322,400 are incorporated herein by reference in their entirety.

The alcohol solvents constitute a large percentage of the total weight of the compositions of the present invention. Illustratively (and not limiting), the alcohol can constitute up to, for example, 90% by weight, of the total weight of the cosmetic stick composition, while still attaining a solid stick.

A second important ingredient in the compositions of the present invention is water (for example, distilled water). Water can be incorporated in the present composition in an amount up to 40% by weight, of the total weight of the composition.

As indicated previously, the soap gel-forming agent forms an essential part of the present invention, and according to the present invention includes, e.g., relatively large amounts of alkali metal salts of $C_{20}$ and/or $C_{22}$ fatty acids (e.g., alkali metal salts of arachidic acid and/or alkali metal salts of behenic acid). Preferred salts are the sodium salts of arachidic and behenic acid (that is, sodium arachidate and sodium behenate). At least 65% by weight, of the total weight of the soap, are the alkali metal salts of $C_{20}$ and/or $C_{22}$ fatty acids (e.g., alkali metal salt of arachidic acid and/or alkali metal salt of behenic acid).

An illustrative carbon-chain-length distribution of the fatty acid component of the alkali metal salts of the fatty acids which are the soap gel-forming agents of the present invention is shown in the following Table 1. In this Table 1, the percentage is the percent by weight, of the alkali metal salt containing the specific fatty acid component, as a percentage of the total weight of the soap in the composition. The distribution shown in Table 1 is illustrative as a preferred range and is not limiting; for example, the soap gel-forming agent according to the present invention can include some alkali metal salt of lauric acid ($C_{12}$ carbon chain length).

TABLE 1

FATTY ACID COMPONENT DISTRIBUTION
IN SOAP GEL-FORMING AGENT

| Carbon-chain-length | % |
|---|---|
| $C_{14}$ | 0–1.0 |
| $C_{16}$ | 5.0–10.0 |
| $C_{18}$ | 18.0–26.0 |
| $C_{20}$ | 32.0–36.0 |
| $C_{22}$ | 33.0–35.0 |

Illustratively, these fatty acid components can be derived from myristic acid ($C_{14}$), palmitic acid ($C_{16}$), stearic acid ($C_{18}$), arachidic acid ($C_{20}$) and behenic acid ($C_{22}$). Generally, the soap gel-forming agent has a white to off-while color, and is a free-flowing granular powder. It is readily soluble in heated solutions of alcohol/glycol mixtures.

An illustrative soap gel-forming agent which can be utilized according to the present invention is sold by RTD Chemicals Corp., of Hackettstown, N.J., under the name RTD Sodium Stearate OP-65. It is constituted by sodium salts of various fatty acids. This composition includes the following fatty acid distribution in the sodium salts, in % by weight of the sodium salt containing the specific fatty acid component, of the total amount by weight of the sodium salts in the composition:

| $C_{14}$ | (myristic) | 0.4 |
|---|---|---|
| $C_{16}$ | (palmitic) | 6.9 |
| $C_{18}$ | (stearic) | 21.8 |
| $C_{20}$ | (arachidic) | 33.3 |
| $C_{22}$ | (behenic) | 33.8 |

This soap gelling agent RTD Sodium Stearate OP-65 has a free fatty acid content of 0.57% by weight, a moisture content of 2.24% by weight, and an ash (as sodium carbonate) content of 16.8% by weight, of the total weight of the composition. RTD Sodium Stearate OP-65 has a titer of 65.4° C.

Depending on the type of stick to be formed (e.g., deodorant stick, insecticide stick, sunscreen stick, etc.), different active ingredients can be incorporated in the composition. Such active ingredients can include biologically active materials such as bacteriostats and fungicides, emollients, ultraviolet absorbers or "sunscreens", talc, etc. Of course, any active ingredient must be stable in the aqueous alkaline environment provided by the sodium stearate/water/alcohol vehicle.

Various active ingredients which can be incorporated in the cosmetic soap-gelled stick composition according to the present invention are disclosed in U.S. Pat. No. 4,322,400, the contents of which have previously been incorporated herein by reference in their entirety. Other active ingredients are disclosed in U.S. Pat. No. 4,382,079, the contents of which also have previously been incorporated by reference herein in their entirety.

A particular cosmetic solid stick composition according to the present invention is a deodorant soap-gelled solid stick composition. Such deodorant soap-gelled solid stick composition would include at least one deodorant active ingredient; these deodorant active ingredients can be those known in the art. Suitable deodorant active ingredients include bacteriostatic quaternary ammonium compounds such as cetyltrimethylammonium bromide, cetyl pyridinium chloride, benzethonium chloride, diisobutyl phenoxy ethoxy ethyl dimethyl benzyl ammonium chloride, N-alkylpyridinium chloride, N-cetyl pyridinium bromide, sodium N-lauroyl sarcosine, sodium N-palmetoyl sarcosine, laroyl sarcosine, N-hyristoyl glycine, potassium N-lauroyl sarcosine and stearyl trimethyl ammonium chloride. Another conventional deodorant material useful in deodorant soap-gelled solid stick compositions according to the present invention is 2-4-4'-trichloro-2'-hydroxydiphenyl ether (Triclosan).

Conventional deodorant active materials, for forming the deodorant soap-gelled solid sticks according to the present invention, are disclosed in previously mentioned U.S. Pat. No. 4,322,400, the contents of which have previously been incorporated herein by reference in their entirety, and in previously discussed U.S. Pat. No. 4,759,924, the contents of which are incorporated herein by reference in their entirety.

Various additional components, such as fragrances and color, can be incorporated in the compositions of the present invention. Such fragrances and colors are those which previously have conventionally been incorporated in cosmetic sticks. Reference is made, for example, to U.S. Pat. No. 5,114,717, the contents of which are incorporated herein by reference in their entirety, for various fragrance compounds which have been incorporated in cosmetic stick compositions. The present invention is not limited to use of such fragrance compounds as in U.S. Pat. No. 5,114,717, but can include fragrance compounds conventionally in use, either for clear or non-clear sticks.

In the following Table 2 is provided an illustrative range for amounts of materials of the cosmetic stick according to the present invention. The soap gel-forming agent is the previously discussed agent including at least 65% by weight of, e.g., alkali metal salt (such as sodium salt) of arachidic and/or behenic acid. These ranges for the ingredients are not limiting of the present invention. In the following Table 2, the presented range is amount by weight, of the total weight of the stick.

TABLE 2

| Ingredient | % |
| --- | --- |
| Propylene Glycol | 20–90 |
| Dipropylene Glycol | 0–60 |
| Soap Gel-Forming Agent | 2–10 |
| Water | 5–40 |
| Fragrance | 0–3.0 |
| Color | Q.S. |

Preferably, compositions according to the present invention include 4%–8% by weight, of the total weight of the composition, of soap gel-forming agent.

The foregoing Table 2 illustrates compositions containing a mixture of alcohols, as the alcohol component of the soap-gelled solid stick composition. Of course, a mixture is not required, and a single alcohol solvent (for example, propylene glycol by itself) can be utilized as the solvent for the soap gel-forming agent, in the composition. While specific alcohols are listed in the foregoing Table 2, compositions according to the present invention, in general, can contain the alcohol in an amount of 20%–90% by weight, of the total weight of the composition, such that the soap gel-forming agent dissolves in the composition during manufacture.

Various other optional components can be included in the compositions according to the present invention. For example, in addition to the alcohol component, water and soap gel-forming agent, and, for example, in addition to the deodorant active ingredient (when the composition is a deodorant soap-based gel stick composition), the compositions can also include chelating agents (for example, ethylenediamine tetraacetic acid), lauramide DEA, antioxidants (e.g., sodium metabisulphite), and other solubilizers as conventionally known in stick formulations. Other optional components conventionally incorporated in soap-gelled solid sticks, and disclosed, for example, in U.S. Pat. No. 4,504,465, the contents of which are incorporated by reference herein in their entirety, and in U.S. Pat. No. 4,759,924, the contents of which have previously been incorporated herein by reference in their entirety, can be included in the composition of the present invention, in amounts as described in these patents.

Attention is also directed to U.S. Pat. No. 4,944,937, the contents of which are incorporated herein by reference in their entirety. This patent discloses various optional "nonactive" components, including emollients and inert filler materials, disclosed as stabilizing agents in cosmetic sticks.

The compositions according to the present invention can be made utilizing conventional techniques. For example, the components, in liquid form, can be mixed together and then poured, for example, into dispensing packages, to be sold to the ultimate consumer. Heating of the components is usually necessary in order to provide the components in liquid form for the necessary mixing. In view of processing at relatively high temperatures, as is conventional in the art, it is desirable to add the fragrances at a relatively late time during mixing, so as to avoid volatilizing off the fragrances.

The gel sticks according to the present invention are used as such sticks are conventionally used by the consumer. Thus, the stick is rubbed, for example, on the area of the body where application is desired. Illustratively, in the case of a deodorant stick for application to the axillary area, the stick is rubbed in the axillary area to deposit the deodorant active agent on the skin. Of course, in use an end of the stick can be exposed out of conventional dispensing packages, and after use retracted back into the dispensing container until the next use.

The following examples further describe and demonstrate embodiments within the scope of the present invention, and demonstrate advantages of the present invention. The examples are given solely for the purpose of illustration and are not to be construed as limitations of the invention. Many variations thereof are possible without departing from the spirit and scope of the present invention.

In the following examples, the stated percentages are percentages by weight, of the stated ingredient, of the total weight of the composition. The names utilized are CTFA designations for the ingredients.

EXAMPLES 1 AND 2

In the following Table 3 are shown two specific deodorant stick compositions within the scope of the present invention, utilizing, as the soap gel-forming agent, the previously set forth RTD Sodium Stearate OP-65 of RTD Chemicals Corp.

TABLE 3

| Ingredients | Example 1 % | Example 2 % |
| --- | --- | --- |
| Propylene Glycol | 70.25 | 70.25 |
| Triclosan | 0.25 | 0.25 |
| Soap Gel-Forming Agent | 7.00 | 7.00 |
| Water | 21.50 | 21.25 |
| Fragrance | — | 1.00 |
| Color | — | Q.S. |
| Titer (° C.) | 63.2 | 61.2 |

COMPARATIVE EXAMPLES 3 AND 4

In the following Table 4 are shown two deodorant stick compositions falling outside the scope of the present invention, in that the soap gel-forming agent does not include the required amounts of salts of $C_{20}$ and/or $C_{22}$ fatty acids. Specifically, the soap gel-forming agent in each of Comparative Examples 3 and 4 is triple-pressed sodium stearate, typically containing about 1% sodium salt of lauric ($C_{12}$) acid, about 2% sodium salt of myristic ($C_{14}$) acid, 53% of sodium salt of palmitic ($C_{16}$) acid, and 44% of sodium salt of stearic ($C_{18}$) acid.

TABLE 4

| Ingredients | Example 3 % | Example 4 % |
| --- | --- | --- |
| Propylene Glycol | 70.25 | 70.25 |
| Triclosan | 0.25 | 0.25 |
| Soap Gel-Forming Agent | 7.00 | 7.00 |
| Water | 21.50 | 21.25 |
| Fragrance | — | 1.00 |

TABLE 4-continued

| Ingredients | Example 3 % | Example 4 % |
|---|---|---|
| Color | — | Q.S. |
| Titer (° C.) | 53.0 | 51.8 |

In comparing Examples 1 and 2 with Comparative Examples 3 and 4, it can be seen that the titer for compositions within the scope of the present invention is higher than that for the comparative examples.

EXAMPLES 5 AND 6

In Examples 5 and 6, a mixture of alcohols was used as the alcohol of the present invention. The soap gel-forming agent was the previously-set-forth RTD Sodium Stearate OP-65 of TRD Chemicals Corp. Moreover, in Example 6 PPG-3-myristyl ether was included in the composition. The compositions of Examples 5 and 6 are shown in Table 5.

TABLE 5

| Ingredient | Example 5 % | Example 6 % |
|---|---|---|
| Propylene Glycol | 23.00 | 23.00 |
| Dipropylene Glycol | 48.00 | 48.00 |
| Triclosan | 0.25 | 0.25 |
| Soap Gel-Forming Agent | 7.00 | 7.00 |
| Water | 20.75 | 21.67 |
| Fragrance | 1.00 | 1.00 |
| Color | Q.S. | Q.S. |
| PPG-3-Myristyl ether | — | 2.00 |
| Titer (° C.) | 62° | 63° |

Examples 5 and 6 show that a mixture of alcohols can be utilized in the solvent system and that PPG-3-myristyl ether can be incorporated in the composition, while still achieving increased titer.

Accordingly, by utilizing a specific fatty acid distribution for the soap gel-forming agent according to the present invention, a gelled stick product can be achieved having a relatively high melting point, and which maintains its physical form and other characteristics even when maintained under relatively high temperatures. Thus, a product which can be stored and/or utilized under hot climatic conditions (for example, in the Far East and/or Latin America) is achieved.

While we have shown and described several embodiments in accordance with the present invention, it is understood that the same is not limited thereto, but is susceptible to numerous changes and modifications as known to one having ordinary skill in the art, and we therefore do not wish to be limited to the details shown and described herein, but intend to cover all such modifications as are encompassed by the scope of the appended claims.

We claim:

1. A gel stick composition comprising at least one alcohol selected from the group consisting of monohydric alcohols and polyhydric alcohols; water; and a soap gelling agent, the at least one alcohol being a solvent for the soap gelling agent, the composition including a sufficient amount of the soap gelling agent to form a solid stick composition, the soap gelling agent including alkali metal salts of fatty acids having carbon chain length within the range of $C_{12}$–$C_{22}$, wherein at least 65% by weight, of the total weight of the soap gelling agent, are alkali metal salts of fatty acids having carbon chain length in a range of $C_{20}$–$C_{22}$, the composition having a melting point greater than 59° C., whereby the gel stick composition can be stored at 120° F. while maintaining size and shape even after three months.

2. The gel stick composition according to claim 1, wherein 100% by weight, of the total weight of the soap gelling agent, are alkali metal salts of fatty acids having carbon chain length in the range of $C_{20}$–$C_{22}$.

3. The gel stick composition according to claim 1, wherein the alkali metal salts of fatty acids having carbon chain lengths in the range of $C_{12}$–$C_{22}$ are sodium salts of fatty acids having carbon chain lengths within the range $C_{12}$–$C_{22}$, with at least 65% by weight, of the total weight of the soap gelling agent, being sodium salts of fatty acids having carbon chain lengths in the range of $C_{20}$–$C_{22}$.

4. The gel stick composition according to claim 3, wherein the composition includes, as a percent by weight of the total weight of the composition, 20%–90% of the at least one alcohol, 2%–10% of the soap gelling agent, and 5%–40% water.

5. The gel stick composition according to claim 4, wherein the composition further includes a deodorant active agent, in a deodorant effective amount, so as to provide a deodorant gel stick composition.

6. The deodorant gel stick composition according to claim 5, wherein the deodorant active agent is a bacteriostat.

7. The deodorant gel stick composition according to claim 6, wherein the bacteriostat is Triclosan.

8. The deodorant gel stick composition according to claim 6, wherein the composition also includes a fragrancing material.

9. The gel stick composition according to claim 4, wherein the composition includes 4%–8% by weight soap gelling agent, of the total weight of the composition.

10. The gel stick composition according to claim 4, wherein the sodium salts of fatty acids include the following distribution of sodium salts of fatty acids, in an amount by weight of the fatty acid salt, as a percentage of total amount of sodium salts of fatty acids:

| sodium salt of fatty acid having carbon chain length indicated below | % |
|---|---|
| $C_{14}$ | 0–1.0% |
| $C_{16}$ | 5.0–10% |
| $C_{18}$ | 18.0–26.0% |
| $C_{20}$ | 32.0–36.0% |
| $C_{22}$ | 33.0–35.0% |

11. The gel stick composition according to claim 4, wherein the at least one alcohol is selected from the group consisting of ethanol, propylene glycol, dipropylene glycol, glycerine and sorbitol, and mixtures thereof.

12. The gel stick composition according to claim 11, wherein the at least one alcohol is a mixture of propylene glycol and dipropylene glycol, the propylene glycol being included in the composition in an amount of 20%–90%, and the dipropylene glycol being included in the composition in an amount up to 60%, by weight, of the total weight of the composition.

13. The gel stick composition according to claim 4, wherein the sodium salts of fatty acids are sodium salts of saturated fatty acids.

14. The gel stick composition according to claim 13, wherein the sodium salts of fatty acids include the following distribution of sodium salts of fatty acids, in amount by weight of the fatty acid salt, as a percentage of total amount of sodium salts of fatty acids:

| sodium salt of fatty acid having carbon chain length indicated below | % |
|---|---|
| $C_{14}$ | 0–1.0% |
| $C_{16}$ | 5.0–10% |
| $C_{18}$ | 18.0–26.0% |
| $C_{20}$ | 32.0–36.0% |
| $C_{22}$ | 33.0–35.0% |

15. The gel stick composition according to claim 4, wherein the soap gelling agent consists of the sodium salts of fatty acids having carbon chain lengths in the range of $C_{12}$–$C_{22}$, with at least 65% by weight, of the total weight of the soap gelling agent, being sodium salts of fatty acids having carbon chain lengths in the range of $C_{20}$–$C_{22}$.

16. The gel stick composition according to claim 1, wherein the composition includes, as a percent by weight of the total weight of the composition, 20%–90% of the at least one alcohol, 2%–0% of the soap gelling agent, and 5%–40% water.

17. The gel stick composition according to claim 16, wherein the alkali metal salts of fatty acids are alkali metal salts of saturated fatty acids.

18. The gel stick composition according to claim 5, wherein the sodium salts of fatty acids include the following distribution of sodium salts of fatty acids, in an amount by weight of the fatty acid salt, as a percentage of total amount of sodium salts of fatty acids:

| sodium salt of fatty acid having carbon chain length indicated below | % |
|---|---|
| $C_{14}$ | 0–1.0% |
| $C_{16}$ | 5.0–10% |
| $C_{18}$ | 18.0–26.0% |
| $C_{20}$ | 32.0–36.0% |
| $C_{22}$ | 33.0–35.0% |

19. The gel stick composition according to claim 1, wherein the composition further includes a deodorant active agent, in a deodorant effective amount, so as to provide a deodorant gel stick composition.

20. The deodorant gel stick composition according to claim 19, wherein the alkali metal salts of fatty acids having carbon chain lengths in the range of $C_{12}$–$C_{22}$ are sodium salts of fatty acids having carbon chain lengths within the range $C_{12}$–$C_{22}$, with at least 65% by weight, of the total weight of the soap gelling agent, being sodium salts of fatty acids having carbon chain lengths in the range of $C_{20}$–$C_{22}$.

21. The deodorant gel stick composition according to claim 20, wherein the sodium salts of fatty acids include the following distribution of sodium salts of fatty acids, in an amount by weight of the fatty acid salt, as a percentage of total amount of sodium salts of fatty acids:

| sodium salt of fatty acid having carbon chain length indicated below | % |
|---|---|
| $C_{14}$ | 0–1.0% |
| $C_{16}$ | 5.0–10% |
| $C_{18}$ | 18.0–26.0% |
| $C_{20}$ | 32.0–36.0% |
| $C_{22}$ | 33.0–35.0% |

22. The deodorant gel stick composition according to claim 21, wherein the alkali metal salts of fatty acids are alkali metal salts of saturated fatty acids.

23. A method of reducing body malodor, comprising the step of applying the composition of claim 22 to axillary regions of a body.

24. A method of reducing body malodor, comprising the step of applying the composition of claim 19 to axillary regions of a body.

25. A method of reducing body malodor, comprising the step of applying the composition of claim 8 to axillary regions of a body.

26. A method of reducing body malodor, comprising the step of applying the composition of claim 5 to axillary regions of a body.

\* \* \* \* \*